US00PP34231P2

(12) United States Plant Patent
Heuger

(10) Patent No.: US PP34,231 P2
(45) Date of Patent: May 10, 2022

(54) ***HELLEBORUS* PLANT NAMED 'COSEH 6200'**

(50) Latin Name: ***Helleborus* x *ericsmithii* X *Helleborus* x *hybridus***
Varietal Denomination: COSEH 6200

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 17/514,316

(22) Filed: Oct. 29, 2021

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Helleborus* plant named 'COSEH 6200', characterized by its upright to outwardly spreading and mounded plant habit; vigorous growth habit; dark green-colored leaves; freely flowering habit; light yellowish green and purplish red bi-colored flowers; and good garden performance.

1 Drawing Sheet

Figure 2:
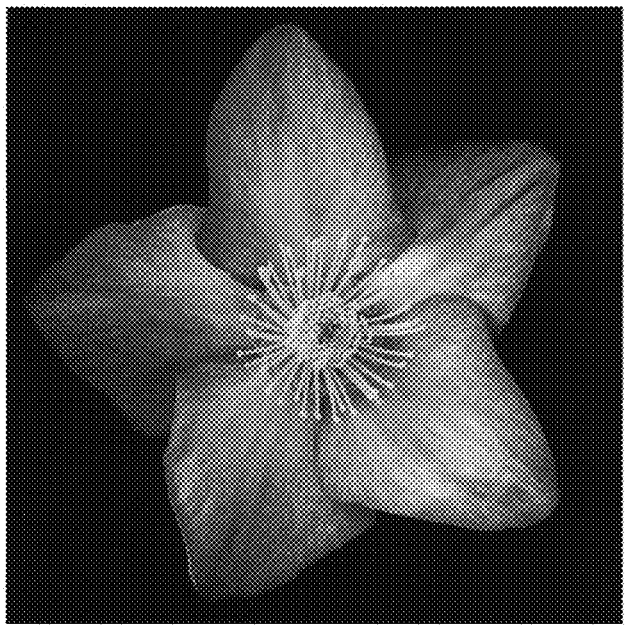

Botanical designation: *Helleborus* x *ericsmithii* X *Helleborus* x *hybridus*.
Cultivar denomination: 'COSEH 6200'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Nov. 30, 2020, application number 2020/3089. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 6200'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in November, 2012 of a proprietary selection of *Helleborus* x *ericsmithii* identified as code number 1843, not patented, as the female, or seed, parent and an unnamed selection of

*Helleborus* x *hybridus*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in November, 2013.

Asexual reproduction of the new *Helleborus* plant by in vitro axillary meristem culture in a controlled environment in Glandorf, Germany since April, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 6200'. These characteristics in combination distinguish 'COSEH 6200' as a new and distinct *Helleborus* plant:

1. Upright to outwardly spreading and mounded plant habit.
2. Vigorous growth habit.
3. Dark green-colored leaves.
4. Freely flowering habit.
5. Light yellowish green and purplish red bi-colored flowers.
6. Good garden performance.

Plants of the new *Helleborus* differ from plants of the female parent selection in the following characteristics:

1. Leaves of plants of the new *Helleborus* are darker green in color than leaves of plants of the female parent selection.

2. Flowers of plants of the new *Helleborus* are light yellowish green and purplish red bi-colored whereas flowers of plants of the female parent selection are yellowish green in color.

Plants of the new *Helleborus* differ from plants of the male parent selection in the following characteristics:

1. Leaves of plants of the new *Helleborus* are darker green in color than leaves of plants of the male parent selection.
2. Flowers of plants of the new *Helleborus* are light yellowish green and purplish red bi-colored whereas flowers of plants of the male parent selection are light pink in color.

Plants of the new *Helleborus* can also be compared to plants of *Helleborus* x *ericsmithii* X *Helleborus* x *hybridus* 'COSEH 4500', disclosed in U.S. Plant Pat. No. 28,293. In side-by-side comparisons, plants of the new *Helleborus* differ primarily from plants of 'COSEH 4500' in the following characteristics:

1. Leaves of plants of the new *Helleborus* are darker green in color than leaves of plants of 'COSEH 4500'.
2. Flowers of plants of the new *Helleborus* are light yellowish green and purplish red bi-colored whereas flowers of plants of 'COSEH 4500' are white in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

Figure 1:
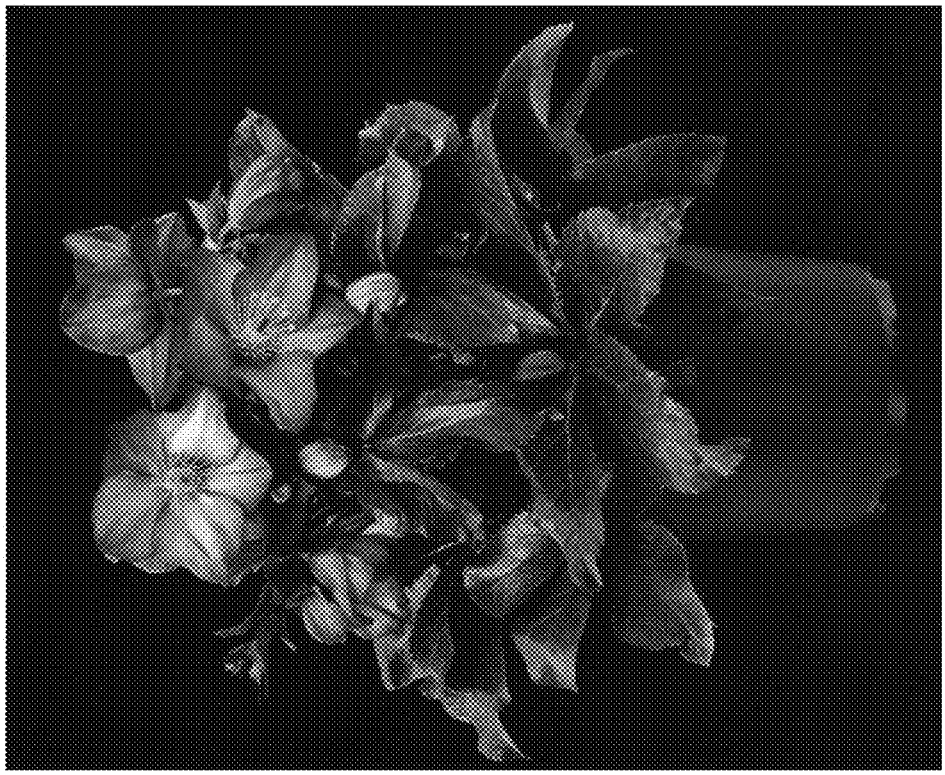

The photograph on the left side of the photographic sheet (FIG. 1) is a side perspective view of a typical flowering plant of 'COSEH 6200' grown in a container.

The photograph on the right side of the photographic sheet (FIG. 2) is a close-up view of a typical flower of 'COSEH 6200'.

DETAILED BOTANICAL DESCRIPTION

The aforementioned photographs and following observations, measurements and values describe plants grown during late autumn and winter in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were eleven months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 6200'.

Parentage:

*Female, or seed, parent*.—Proprietary selection of *Helleborus* x *ericsmithii* identified as code number 1843, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from about 4° C. to 15° C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to outwardly spreading and mounding plant habit with flowers held above the foliar plane; plant shape, roughly flattened globular; vigorous growth habit and moderate growth rate.

*Plant height, soil level to top of foliar plane*.—About 21.8 cm.

*Plant height, soil level to top of flowers*.—About 41.4 cm.

*Plant diameter* (*area of spread*).—About 45.6 cm.

Leaf description:

*Arrangement*.—Leaves arranged in a basal rosette; leaves palmately compound with typically five leaflets per leaf or occasionally, six to seven.

*Leaf length*.—About 27.3 cm.

*Leaf width*.—About 30.3 cm.

*Leaflet length*.—About 16.6 cm.

*Leaflet width*.—About 8.6 cm.

*Leaf shape*.—Palmate; roughly reniform in outline.

*Leaflet shape*.—Elliptic to obovate.

*Leaflet apex*.—Acute.

*Leaflet base*.—Attenuate.

*Leaflet margin*.—Serrate; younger leaves not undulate; older leaves coarsely undulate.

*Leaflet texture and luster, upper surface*.—Smooth, glabrous; coriaceous; moderately glossy.

*Leaflet texture and luster, lower surface*.—Smooth, glabrous; coriaceous; slightly glossy.

*Leaflet venation pattern*.—Pinnate.

*Leaflet color*.—Developing leaflets, upper surface: Close to NN137B; midvein at the base, close to 183D. Developing leaflets, lower surface: Close to 147B slightly tinged close to N186C; venation, close to 187A. Fully developed leaflets, upper surface: Darker than between 147A and N189A; venation, close to 144A and towards the base, close to 200A. Fully developed leaflets, lower surface: Close to 147B; towards the margins, slightly tinged close to N186C; venation, close to between N186C and 200A.

*Petioles*.—Length: About 14.8 cm. Diameter: About 6 mm to 7 mm. Strength: Strong. Texture and luster, upper and lower surfaces: Smooth, glabrous; slightly glossy. Color, upper surface: Close to 146B heavily covered with fine dots, close to N186C. Color, lower surface: Close to 146B heavily covered with fine dots, close to between N186C to 200A.

Flower description:

*Flower shape and habit*.—Rotate flowers; flowers slightly bowl- shaped; flowers arranged in panicles; freely flowering habit with numerous flowers developing per plant during the flowering season; flowers face mostly outwardly to nodding.

*Fragrance*.—None detected.

*Natural flowering season*.—Plants begin flowering about ten months after planting; plants flower naturally from early winter into the winter in Germany.

*Flower longevity on the plant*.—About ten days; sepals persistent, other flower parts are not persistent.

*Flower buds*.—Length: About 1.9 cm. Diameter: About 1.2 cm. Shape: Ovate. Texture and luster: Smooth, glabrous; matte. Color: Close to 145C; towards the apex, tinged with close to 71A; venation, close to 185B.

*Inflorescence height* (*including peduncle*).—About 35.6 cm.

*Inflorescence diameter*.—About 20.3 cm.

*Flower diameter*.—About 8.9 cm by 8.9 cm.

*Flower depth*.—About 2.8 cm.

*Petals*.—All petals are transformed into nectaries.

*Sepals*.—Quantity and arrangement: About five, arranged in a single whorl. Length: About 4.6 cm. Width: About 4.2 cm. Shape: Broadly obovate, slightly concave. Apex: Broadly and bluntly acute to slightly obtuse. Base: Broadly cuneate. Margin: Entire; slightly undulate. Texture and luster, upper surface: Smooth, glabrous; matte. Texture and luster, lower surface: Smooth, glabrous; slightly glossy. Color: When opening, upper surface: Close to 157A; towards the margins, close to 155B; towards the apex, tinged close to 72A to 72B; towards the base, close to 145C; venation, close to 186C. When opening, lower surface: Close to 199D; towards the margins, close to 157B to 157C; towards the apex, strongly tinged close to 71A to 71B; towards the base, tinged with close to 197B; venation, close to 185C. Fully opened, upper surface: Close to between 150D and 160C; towards the apex and margins, strongly tinged close to 186A, 186B and N186D; with subsequent development, color becoming closer to between 146D and 147C, and towards the apex and margins, strongly tinged close to 187B. Fully opened, lower surface: Close to 177D tinged with close to 182C and 182D; towards the apex and margins, strongly tinged close to 186A and N186D; venation, close to N186D; with subsequent development, color becoming closer to 187B, center, tinged close to 146B and venation, close to N186D.

*Flower bracts*.—Quantity per flower: Typically one or two. Length: About 9.1 cm. Width: About 5.5 cm. Shape: Ovate. Apex: Acute to apiculate. Base: Truncate. Margin: Entire to serrate at the top third. Color, upper surface: Slightly darker than close to between NN137A and 147A; at the base, close to 144A. Color, lower surface: Close to between 147A and 147B; towards the margins, tinged close to N186C; midvein, slightly darker than N186C.

*Peduncles*.—Length: About 27.8 cm. Diameter: About 8 mm to 11 mm. Aspect: About 12.5° from vertical. Strength: Strong. Texture and luster: Smooth, glabrous; slightly glossy. Color: Close to 147C to 147D and heavily covered with fine dots, close to between N186C and 200A with a higher density of dots towards the base.

*Pedicels*.—Length: About 5.8 cm. Diameter: About 2 mm. Aspect: About 10° to 30° from peduncle axis. Strength: Moderately strong. Texture and luster: Smooth, glabrous; slightly glossy. Color: Close to 145A.

*Reproductive organs*.—Stamens: Quantity per flower: About 50. Filament length: About 1.8 cm. Filament color: Close to 157A. Anther shape: Double and broadly reniform; basifixed. Anther size: About 2 mm by 2.5 mm. Anther color: Close to 151C. Pollen amount: Scarce. Pollen color: Whitish. Pistils: Quantity per flower: About five. Pistil length: About 1.2 cm. Stigma diameter: About 0.3 mm. Stigma shape: Club-shaped. Stigma color: Close to 150D. Style length: About 1.15 cm. Style color: Close to 184B. Ovary color: Close to 145B. Nectaries (transformed petals): Quantity per flower: About 13. Length: About 1.1 cm. Diameter: About 3.5 mm. Shape: Tubular, moderately flattened. Texture and luster, inner and outer surfaces: Smooth, glabrous; slightly glossy. Color, immature, inner surface: Close to N144D. Color, immature, outer surface: Close to N144D; at the apex, close to 145A. Color, mature, inner surface: Close to N144A; at the apex, close to 151D; venation, similar to lamina colors; with subsequent development, close to N144A and at the apex, close to 153C. Color, mature, outer surface: Close to 146D; at the apex, close to 151C to 151D; venation, similar to lamina colors; with subsequent development, close to 146D and at the apex, close to 153C to 153D.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 6200' as illustrated and described.

* * * * *